US008478539B2

(12) United States Patent
Sieracki

(10) Patent No.: US 8,478,539 B2
(45) Date of Patent: Jul. 2, 2013

(54) SYSTEM AND METHOD FOR NEUROLOGICAL ACTIVITY SIGNATURE DETERMINATION, DISCRIMINATION, AND DETECTION

(76) Inventor: Jeffrey M. Sieracki, Silver Spring, MD (US)

(*) Notice: Subject to any disclaimer, the term of this patent is extended or adjusted under 35 U.S.C. 154(b) by 756 days.

(21) Appl. No.: 12/466,114

(22) Filed: May 14, 2009

(65) Prior Publication Data

US 2010/0016752 A1 Jan. 21, 2010

Related U.S. Application Data

(63) Continuation-in-part of application No. 11/387,034, filed on Mar. 22, 2006, and a continuation-in-part of application No. 10/748,182, filed on Dec. 31, 2003, now Pat. No. 7,079,986.

(60) Provisional application No. 61/053,026, filed on May 14, 2008.

(51) Int. Cl.
*G01N 33/48* (2006.01)
*A61B 5/04* (2006.01)

(52) U.S. Cl.
USPC ............................................ 702/19; 600/544

(58) Field of Classification Search
None
See application file for complete search history.

(56) References Cited

U.S. PATENT DOCUMENTS

| | | | | |
|---|---|---|---|---|
| 5,502,764 | A | 3/1996 | Naccache | |
| 5,699,121 | A | 12/1997 | Zakhor et al. | |
| 5,764,921 | A | 6/1998 | Banham et al. | |
| 6,016,546 | A | 1/2000 | Kephart et al. | |
| 6,587,507 | B1 | 7/2003 | Chui et al. | |
| 6,625,213 | B2 | 9/2003 | Bottreau et al. | |
| 6,628,300 | B2 | 9/2003 | Amini et al. | |
| 6,944,222 | B2 | 9/2005 | Van Der Schaar | |
| 6,985,526 | B2 | 1/2006 | Bottreau et al. | |
| 7,003,039 | B2 | 2/2006 | Zakhor et al. | |
| 7,006,567 | B2 | 2/2006 | Frossard et al. | |
| 7,120,587 | B2 | 10/2006 | Heusdens et al. | |
| 7,245,659 | B2 | 7/2007 | Sekiguchi et al. | |
| 7,526,645 | B2 | 4/2009 | Miyazaki et al. | |
| 7,747,325 | B2 * | 6/2010 | Dilorenzo | 607/45 |
| 2005/0096710 | A1 * | 5/2005 | Kieval | 607/45 |

OTHER PUBLICATIONS

Sieracki et al., "Greedy adaptive discrimination: component analysis by simultaneous sparse approximation," (Proc. of SPIE vol. 5914, 5914R (2005) pp. 1-9).*

Husoy et al. "Removal of Cardiopulmonary Resuscitation Artifacts From Human ECG Using an Efficient Matching Pursuit-Like Algorithm" (IEEE Transactions on Biomedical Engineering, vol. 49 (2002) pp. 1287-1298).*

Leviathan et al. "Simultaneous Approximation by Greedy Algorithms," Industrial Mathematics Institute, Research Report 2003:02, pp. 1-17.*

Leviathan et al. "Simultaneous Greedy Approximations in Banach Spaces," Industrial Mathematics Institute, Research Report 2003:26, pp. 1-18.*

Mallet, S., et al.; "Matching pursuits with time-frequency dictionaries"; IEEE Transactions on Signal Processing, vol. 41, No. 12, pp. 3397-3415; 1993.

Preprint of published Davis, G., et al.; "Adaptive greedy approximations", Journal of Constructive Approximations, vol. 13, pp. 57-98; 1997.

Sadler, B., et al.; "Optimal and wavelet-based shock wave detection and estimation", J. Acoust. Soc. Am.; vol. 104, Issue 2, pp. 955-963; Aug. 1998.

Bultan, A.; "A Four-Parameter Atomic Decomposition of Chirplets"; IEEE Transactions on Signal Processing; vol. 47, No. 3, pp. 731-745; Mar. 1999.

Bergeaud, F., et al.; "Matching Pursuit of Images"; pp. 1-16; Copyright 1995 by Academic Press, Inc.

Preprint of Published Leviatan, D., et al.; "Simultaneous approximation by greedy algorithms"; Advances in Computational Mathematics (2006) 25: 73-90; Springer 2006.

* cited by examiner

*Primary Examiner* — Anna Skibinsky
(74) *Attorney, Agent, or Firm* — Rosenberg, Klein & Lee

(57) ABSTRACT

A system and method are provided for automatically correlating neurological activity to a predetermined physiological response. The system includes at least one sensor operable to sense signals indicative of the neurological activity, and a processing engine coupled to the sensor. The processing engine is operable in a first system mode to execute a simultaneous sparse approximation jointly upon a group of signals sensed by the sensor to generate signature information corresponding to the predetermined physiological response. The system further includes a detector coupled to the sensors, which is operable in a second system mode to monitor the sensed signals. The detector generates upon selective detection according to the signature information a control signal for actuating a control action according to the predetermined physiological response.

20 Claims, 10 Drawing Sheets

Where $$f^i = \sum_n a_n^i g_n^i$$

$$g_n^i = g(s_n^i, u_n^i, \xi_n^i, \phi_n^i) \in D$$

$$i \in [1, m]$$

$$n \in N$$

Component Energy Density

Recovered Detail

SYSTEM AND METHOD FOR NEUROLOGICAL ACTIVITY SIGNATURE DETERMINATION, DISCRIMINATION, AND DETECTION

RELATED APPLICATION DATA

This Application is based on Provisional Patent Application No. 61/053,026, filed 14 May 2008, as a Continuation-In-Part of patent application Ser. No. 11/387,034 filed 22 Mar. 2006, which is a Continuation-In-Part of patent application Ser. No. 10/748,182 filed 31 Dec. 2003, now U.S. Pat. No. 7,079,986.

BACKGROUND OF THE INVENTION

The present invention is directed to a system and method for pattern and signal recognition and discrimination. More specifically, the present invention is directed to a system and method for brain and peripheral nerve and muscle signal processing, and more particularly to sensing and processing systems and methods in which one or more transducers register a signal representative of electrical, metabolic, or other activity in the brain and associated body structures. Further, the present invention is directed to systems and methods whereby certain signals or classes of signals may be effectively discriminated from one another for various purposes, such as for medical, diagnostic, or computer-brain interface purposes.

This invention utilizes certain aspects of methods and systems previously disclosed in U.S. patent application Ser. No. 10/748,182, (now U.S. Pat. No. 7,079,986) entitled "Greedy Adaptive Signature Discrimination System and Method" and that filing is hereby incorporated by reference and hereinafter referred to as [1], as well as certain aspects of methods and systems previously disclosed in U.S. patent application Ser. No. 11/387,034, entitled "System and Method For Acoustic Signature Extraction, Detection, Discrimination, and Localization" that is hereby incorporated by reference and hereinafter referred to as [2].

SUMMARY OF THE INVENTION

It is an object of the present invention to provide a system and method for automatically correlating neurological activity to a predetermined behavioral activity, brain state/condition, or other such physiological response.

It is another object of the present inventions to provide a system and method for sensing neurological activity of a subject and responsively actuating a control action corresponding to the predetermined physiological response.

These and other objects are attained by a system and method formed in accordance with the present invention. The system includes at least one sensor operable to sense signals indicative of the neurological activity, and a processing engine coupled to the sensor. The processing engine is operable in a first system mode to execute a simultaneous sparse approximation jointly upon a group of signals sensed by the sensor to generate signature information corresponding to the predetermined physiological response. The system further includes a detector coupled to the sensors, which is operable in a second system mode to monitor the sensed signals. The detector generates upon selective detection according to the signature information a control signal for actuating a control action according to the predetermined physiological response. Depending on the intended application, the predetermined physiological response in various embodiments may include certain behavioral activity or certain brain state or condition.

DETAILED DISCLOSURE OF THE PREFERRED EMBODIMENTS

Figure 1:
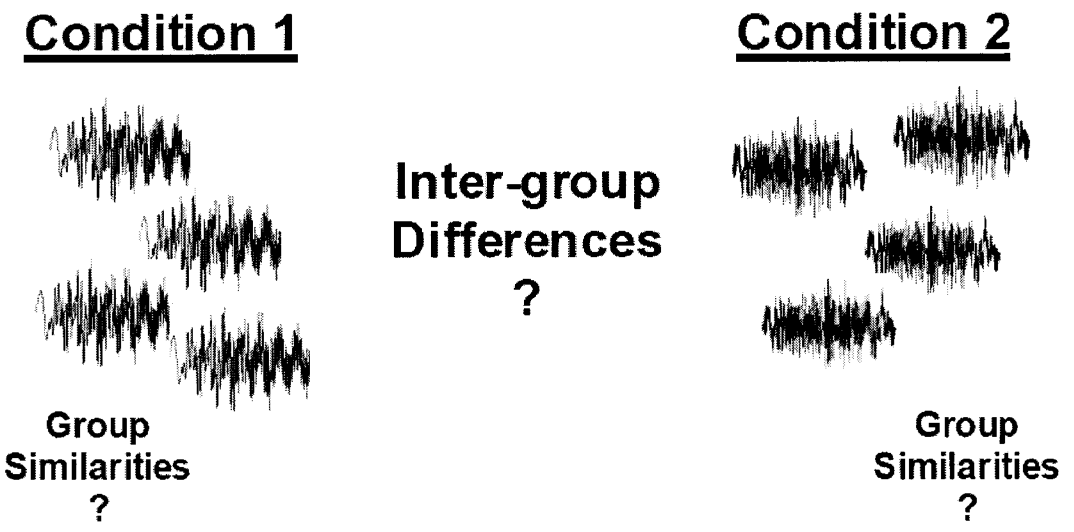
FIG. 1 is a schematic diagram illustrating distinguishable signal groups obtained under different conditions.

Brain signals may be measured by a host of suitable means well known in the art, including EEG, ECoG, MEG, fMRI, and others. They may also be measured remotely or indirectly through peripheral nerve or muscle activity. Depending on the intended application, signals of interest may represent time-course events, spatially distributed patterns, or combinations of the two. These signals are generally studied in correlation with behavioral activity in order to map the measured brain activity to a particular behavioral activity. For example, activity in a specific region of the brain during word reading may be used to determine involvement of that brain region in the word reading process. Measurable activity (electrical, metabolic, magnetic, etc.) is typically well removed from the micro-level dynamics going on in the brain; therefore, it often becomes difficult to discriminate meaningful activity from meaningless activity.

A "signature" is a pattern within a signal or data stream that may be associated with a condition of interest in the signal generating system. There are numerous applications for brain activity signature detection and discrimination. For example, signals may indicate various states or conditions such as: sleep, epilepsy, anxiety, degrees of anesthesia, and degrees of attention. Signals may also indicate the occurrence—or impending occurrence—of an event, such as: moving an arm, thinking of a specific idea, speaking, and so forth. Discerning signatures for such signals is useful in computer-brain interfacing applications and the like. Brain signals may also be used to identify their source, both in terms of the location within a particular individual's brain for mapping purposes and identification of one individual's brain signals, as differentiated from another's brain signals.

A usable method generally addresses several related goals: the translation of signals into a representation that allows for their manipulation and comparison; comparison of classes of signals to ascertain and extract characteristic signatures; creation of a detector/classifier to recognize signatures in a way that is robust in view of noise and environmental factors; and localization of detected signatures, if necessary. Reference [1] discloses a suite of methods that can accomplish these goals. Reference [2] discloses a generalized processing scheme extending [1]. In accordance with the present invention, certain approaches to brain signal analysis are provided, along with refinements and additional complimentary methods for use in deployable sensors and processors.

In accordance with an exemplary embodiment of the present invention, a method is provided for processing, analyzing, and comparing brain signals in order to facilitate signature detection. The process preferably begins with collecting brain data that is representative of the signals to be detected. The data is normalized so that individual recordings are approximately comparable, and divided into classes. Each class preferably comprises multiple recordings of a particular event or state of interest. A simultaneous sparse approximation is performed on the data, and, if necessary, one or more parametric "mean" representations are generated for signal classes. In certain embodiments, the method incidentally corrects for and removes parameter jitter between signals. The parametric mean representations that may be thus derived ([1] [2]) to include a collection of time-frequency atoms that represent a "typical" signal in the class.

The parametric mean representations may, in some embodiments, be compared to each other in order to further reduce the dimensionality of the signal representations. For example, only those signal components that distinguish between classes may be kept, and other components common to the classes, generally, may be discarded. In certain embodiments, the components may be diagonalized in order to achieve an orthogonal representation. In any case, by noting components that distinguish between signal classes, and/or noting class-typical values of components that are common among multiple signal classes, the method and system in accordance with an aspect of the present invention establishes unique signature discrimination criteria.

Numerous alternative embodiments of a detector may be employed in accordance with the present invention, to utilize the newly ascertained signature information. In certain embodiments, a deployed sensor will utilize extracted parameters from the signal signatures to define a spectral filter corresponding to each signature. In other embodiments, the deployed sensor will directly utilize the collection of atoms that describe the signature, comparing these to a similar analysis of any new signal. One embodiment of such a detector is to generate a dictionary that contains compound atoms representative of the signatures of interest and utilize a nearest neighbor metric. In certain embodiments, the parametric mean representations contain sufficient information to reconstruct an "average" signature signal in the original time domain. This reconstructed signature signal or collections of signature components may be compared with any new signals by suitable measures set forth in [1] and [2], or by any suitable means known in the art.

Combining detection and localization presents additional challenges. In accordance with one exemplary embodiment of the present invention, such detection and localization are carried out sequentially. A signal recorded by one or more sensors is preferably normalized and compared to the signature database. If multiple transducers establishing multiple data channels are employed, numerous operational configurations may be realized. In a first configuration, each channel is compared individually to the database and a weighted decision metric yields a final determination. In a second configuration, the signals are cross-correlated for phase alignment, and a summed (or averaged) signal resulting therefrom is compared to the database. In a third configuration, the signals are analyzed using a GAD sparse approximator, whereby the signals are phase aligned and de-jittered by taking a parametric "average." The "average" signal is then correlated to a predetermined dictionary. Extracted signature patterns may preferably be temporal, spectral, or both.

There are benefits and drawbacks to each configuration. The third configuration offers specific advantages, for example, when distributed sensors are located only approximately, or have free running data clocks, both of which introduce unknown variation into timing and position information. Once a signature is determined to be present and (if necessary) properly classified, it is located within the recordings from each individual channel. The relative phase, timing, and energy (volume) information is analyzed across channels to localize the signal's source. The signal may be located within each channel by any suitable means known in the art, including for example cross-correlation or pattern search. The signal may also be located, in certain embodiments, by extracting parameters directly from the GAD sparse approximator output rather than performing an additional calculation. Below is a brief summary of the GAD processing disclosed in more detail in [1] and [2], aspects of which are incorporated in the given embodiments.

GAD Summary

Figure 3:
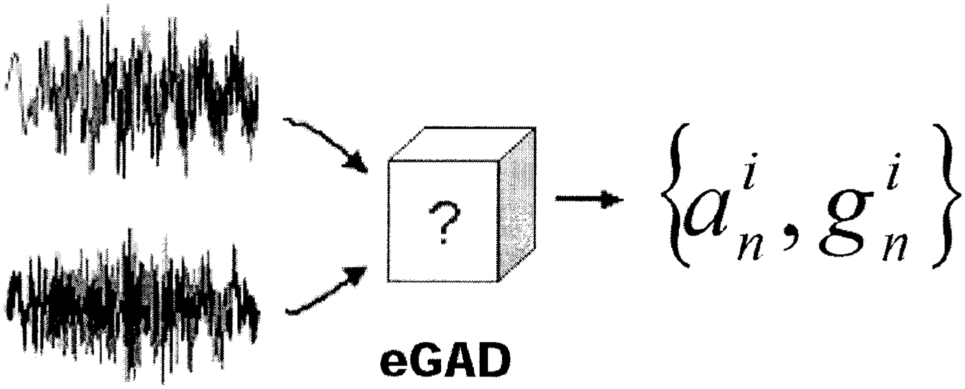
FIG. 3 is a schematic diagram illustrating a joint analysis of a plurality of signal groups carried out in accordance with an exemplary embodiment of the present invention to obtain a transformed representation thereof.

The main elements of the GAD approach include a "GAD engine," comprising a Simultaneous Sparse Approximator ("SSA"), a structure book memory system, and one or more discrimination functions that operate on the structure books. The SSA takes as input a plurality of signals and produces a structure book for each signal. The output of the SSA comprises one or more structure books selected or otherwise suitably processed as illustratively disclosed in [1] and [2]. A structure book describes a linear decomposition of the signal and comprises a list of coefficients and a corresponding list of atoms for the decomposition. For example, the signal f(t) may be expressed as:

$$f(t)=a_0g_0(t)+a_1g_1(t)+\ldots+a_ng_n(t)+R,$$

where $a_i$ represent the coefficients and $g_i(t)$ represent the atoms, or prototype-signals of the decomposition, and R represents the residual error (if any) after n+1 terms. If R=0 then the representation is exact, otherwise the decomposition is an approximation of f(t). One way to write the structure book is as a set of ordered pairs, ($a_i$, $g_i(t)$); however, the atom $g_i(t)$ itself need not be recorded. Descriptive information stored in the structure book may comprise the atom itself, a coded reference to the atom, or one or more parameters that uniquely define the atom (providing benefits such as memory efficiency, speed, and convenience of accessing the atom and/or its properties). The atoms $g_i(t)$ belong to a predetermined dictionary D of prototype signal elements, and are each preferably expressed in the exemplary embodiment (as illustrated in FIG. 3) as a function of scale, position, modulation, and phase parametric elements ($s^i_n$, $u^i_n$, $\xi^i_n$, $\phi^i_n$) obtained from the dictionary D.

The dictionary D is preferably provided as an intrinsic element of the SSA. In certain SSA implementations, the dictionary D may be implicit rather than a distinct separable component. In general, structure books are created relative to a dictionary D, and subsequent operations are performed based on this implicit relationship. A structure book may be recast into another representation by suitable mathematical projection operations known to those skilled in the art, in which case the elements $g_i(t)$ and the coefficients $a_i$ used in the structure book may change. In some cases, these new elements $g_i(t)$ may belong to the original dictionary D, in other cases a new dictionary may be used.

The SSA produces structure books for each signal in the input collection of signals, such that the atoms of any structure book may be compared directly to those of any other. In the simplest case, the atoms may be identical for all signals in the collection. However, GAD SSA, as described in [1] and [2], is also able to produce atoms that are "similar" as judged by the given processing rather than identical. This feature is advantageous in many implementations because it allows the processing to automatically account for noise, jitter, and measurement error between the signals.

Processes that produce similar simultaneous approximations for a group of signals may be substituted with appropriate adjustments. The atoms selected will vary depending upon the SSA implementation. Furthermore, the output of any such SSA may be further processed (e.g., to orthogonalize the atoms in the structure books) without departing from the spirit and scope of the present invention.

Generally, a GAD SSA permits the range of "similarity" between atoms across structure books to be controlled by setting a search window for each of the parameters of the dictionary. The windows may be fixed in advance for each parameter, or may be adapted dynamically. One adaptation that is sensible, for example, is to adjust the search window according the classical uncertainty principal. That is, appropriate search windows (and step sizes) for time and frequency may be co-adjusted based on the time or frequency spread of the atom. The variation serves to associate similar-though-not-identical atoms in an automatic fashion. Numerous windowing schemes will fall within the general mechanism.

A detail of the SSA implementation is the dictionary from which atoms may be selected. For illustrative purposes, certain embodiments herein disclosed utilize a Gabor dictionary such as referenced in [1] and [2], which comprises modulated, translated, and scaled Gaussians, combined with Fourier and Dirac delta bases. This exemplary dictionary does not limit the scope of the present invention, and other reasonable collections of prototype signals may be substituted, including in certain embodiments a dictionary of random prototype signals. In other embodiments, the dictionary may be orthogonal, such as one having a Fourier basis, or not. It may be redundant, such as one having a collection of wavelet packet bases. It may also be highly redundant, as is the Gabor dictionary. Certain advantages of speed may be realized with sparser dictionaries; however, redundancy tends to increase the SSA's ability to generate a sparse approximation that does not oversimplify. In this case "sparse approximation" means an approximation that is reasonably close to the signal while containing relatively few terms in comparison to the length of the signal.

Exemplary embodiments of the present invention are discussed herein in terms of time varying electrical signals, such as those recorded by ECoG, EEG, MEG, or EMG. However, various embodiments of the present invention are directly applicable to spatial signal patterns as well as to signals derived from other measures such as single unit recordings, metabolic measures such as fMRI, PET, and the like.

Estimated parametric Greedy Adaptive Discrimination (eGAD) is a method disclosed in [1] for signal-ensemble component analysis. The method combines a GAD processing engine as described in [1] and [2] with manipulations in the output parameter space, also described in those disclosures. Not only is it robust against time (or spatial) jitter and additive noise, eGAD tends to resolve more time-frequency (time-space) detail than other methods known in the art, and retain sufficient information to allow suitable time-domain reconstruction of signature activity.

An exemplary embodiment of the present invention is applicable to the automated analysis of human electrocortigraphic (ECoG) recordings to identify characteristic activity patterns associated with certain behavioral activities, such as a simple first-clenching motor task. Electrocorticography (ECOG) comprises direct recording of electrical signals from the brain surface. Brain activity data is thereby collected from a grid of electrodes placed surgically on the subject's brain. Predictive analysis of brain activity is supported by reliably correlating these electrical signals with behavioral tasks. The behavioral task associated with acquired ECoG data in the given example is a cued voluntary muscle contraction, in which a subject clenches his/her first in response to computer-generated cues. This defines an active condition which is subsequently compared to data corresponding to a passive baseline condition.

Each trial recording may be synchronized, for instance, to the onset of a visual cue. One cannot expect precise time alignment of the ensemble signals since they are biological in origin and subject to such factors as human reaction time variation. The relationship between ECoG and an underlying activity cannot easily be predicted due to the enormous complexity of a subject's biological system. Hence, in empirically determining the electrical signature of behavioral activity, it is preferable to minimize assumptions as to the nature of the signature, potentially allowing time, phase, amplitude, and frequency to vary due to uncontrolled factors. The GAD based methods used in accordance with the present invention advantageously minimize the effects of such uncontrollable data variations.

Figure 4:
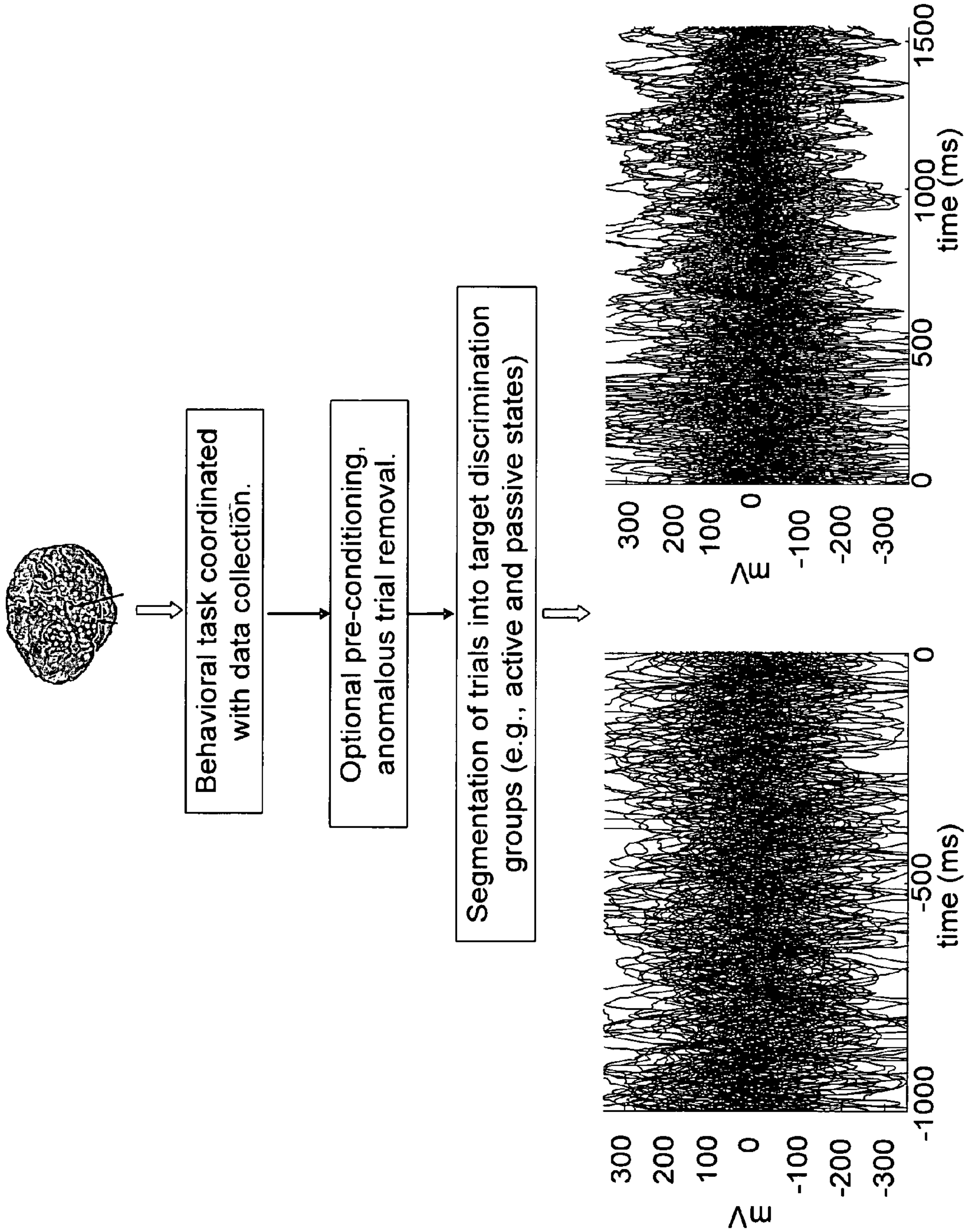
FIG. 4 is a schematic diagram illustrating a general progression of functional processes for developing signature information by which to discriminate neurological activity in accordance with an exemplary embodiment of the present invention.

In an exemplary embodiment, such as illustrated in FIG. 4, data is collected from a grid of electrodes placed surgically on the subject's brain. In alternate embodiments, the activity may be recorded by other suitable measures, such as by applying one electrode, several electrodes, or a grid of electrodes to the surface of the subject's head (EEG), by magnetic detection of currents, by optical dye tracking, and so forth. In other embodiments, the data may be formed by metabolic or some other time varying signal. In still other embodiments, the signal may be spread across space rather than time varying, or may be both time and space varying. What is disclosed is but one working illustration of the invention in one exemplary embodiment. The present invention is not limited to such exemplary embodiments.

The signature discovery problem generally seeks to selectively ascertain those characteristics of given signals that best discriminate between two or more groups of those signals. FIG. 1 illustrates the general questions that arise, which are addressed by the methods disclosed in [1] and [2]. According to these methods, the signature discovery problem is addressed by preferably finding an appropriate representation space in which to compare signal groups.

Figure 2:
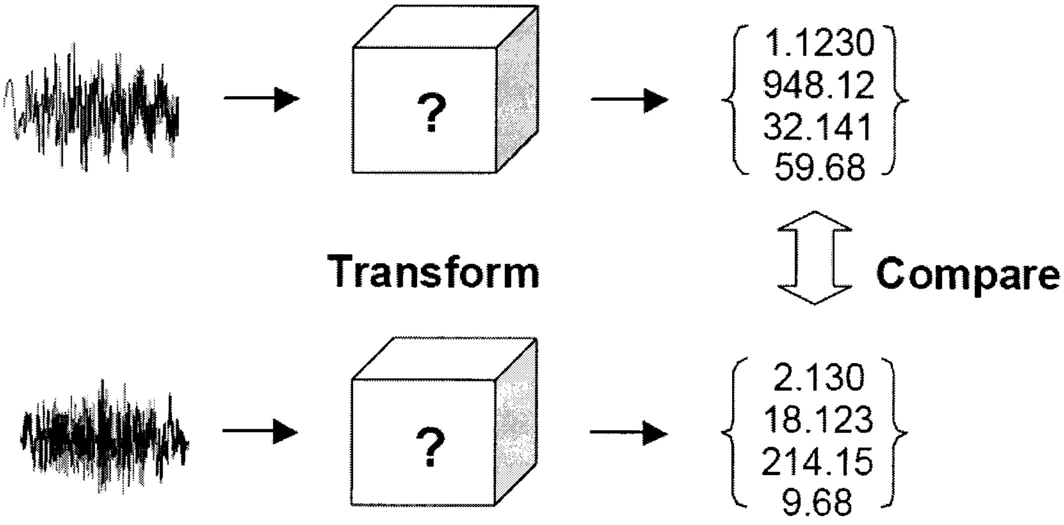
FIG. 2 is a schematic diagram generally illustrating a transformation process respectively applied to signal groups to obtain transformed representations thereof.

FIG. 2 illustrates the application of a suitable transform of the signal groups into appropriate representations, so as to make their comparative analysis natural. After the signals are transformed, the disclosed methods enables a manageable collection of numerical values to be evaluated using tools discussed in [1] and [2], which values contain the salient information from the respective signal groups. Assumptions in making the transformation are minimized—by preferably applying an adaptive sparse approximation which simultaneously well represents all the signals in a compact way that makes comparisons natural. The GAD process employed in this approximation exploits weak redundancy in the ensemble using a modified simultaneous matching pursuits type greedy approach to extract parameterized equivalence classes of signal components from the signals (indicated as a set$\{f_i\}$).

FIG. 3 illustrates the joint analysis which occurs in the GAD process, whereby the signals of a grouped set are simultaneously transformed. The resulting structures of information for the respective groups—such as a set of coefficients for signal components in each group—are then compared. Details are further disclosed in [1] and [2]. As discussed in [2], while GAD is used in the preferred embodiment, other methods of sparse approximation may be applied in accordance with this aspect of the present invention. Various modifications and applications of the present invention will be clear to those versed in the art upon understanding this invention together with the teachings of [1] and [2].

In the illustrated embodiment, ECoG signal data is collected from motor regions of the brain during a cued first-clenching task. FIG. 4 illustrates the basic process. Generally, multiple trials are collected in order to build a consistent picture of the underlying activity. Each trial is loosely synchronized to a fixed time point, in this case the onset of a visual cue displayed on a computer screen. In addition, the subject's response is monitored by recording EMG (electrical muscle activity) in the arm to confirm the subject's actions. Trials that are inconsistent or exhibit anomalies are discarded. The weak time correlation is improved upon in accordance with the present invention (as discussed in [1] and [2]) to extract tightly correlated patterns from the noisy and jittered data. This is in contrast to conventional approaches where tight behavioral time correlation is required to obtain reliable results.

Signals from each electrode will in certain embodiments be preconditioned. The preconditioning may include re-referencing the signals by subtractive processing to any of the available additional electrodes or to an average reference signal. This technique may be used to control for spatially diverse signals in order to consider only the more local of their components. It may also be used to control for common mode noise. In addition, levels may be normalized to maximize processing headroom. Under certain circumstances pre-filtering or de-noising using any suitable technique known in the art may be effected before the disclosed methods are applied.

The ensemble of trial signals is separated into baseline and active time periods (as illustrated at the bottom of FIG. 4). The baseline period is that time prior to the onset of cue delivery to the subject—during which the subject is in a resting, attentive state. The active period is that time following onset of cue delivery—during which the subject takes responsive action. The resulting groups of signals form the basis of comparison. Generally, the signature determination process then involves discovering what has changed from one group of signals to the other.

The GAD process constructs a parameterized sparse representation space for the signal ensemble. Estimates of source signal components are recovered by reducing each equivalence class to a best estimate of the generating atom. This is accomplished in the illustrated embodiment using a Gabor dictionary parameterized by $\gamma=(s, u, \xi)$, where s, u, $\xi$ correspond respectively to scale, position, modulation, as discussed in [1]. The position parameter is allowed to vary in the GAD process, while closer matches of the other parameters are demanded. This allows the process to factor in human reaction time and eventually discover signatures that might otherwise be obscured by time-based blurring.

Figure 5:
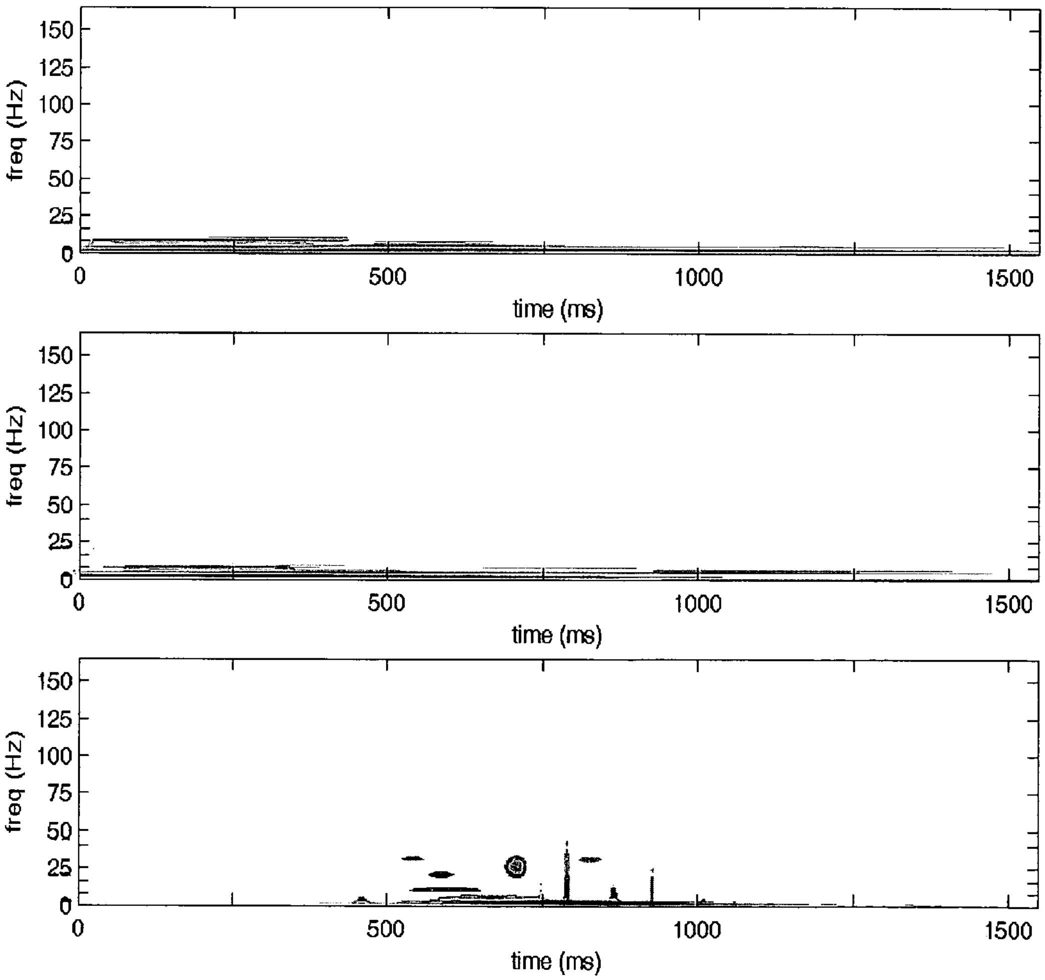
FIG. 5 is a set of graphic plots of time-frequency energy density obtained for signal groups processed within various data channels in accordance with an exemplary embodiment of the present invention.

One may then extract a representative atom for each equivalence class by examining the given parameter space. A parametric mean is determined in accordance with the teachings of [1], [2] to estimate common underlying source elements in ECoG signals occurring under the active-condition. Examples of Wigner Time-Frequency (T-F) energy density plots for the raw extracted component atoms are illustrated in FIG. 5. Darker regions of the time-frequency plane represent areas of higher energy. The uppermost plot corresponds to a first ECoG channel, while the intermediate plot corresponds to a second ECoG channel from the same task and grid. The last plot corresponds to EMG data from the arm of the patient, analyzed by the same methods.

Other alternate embodiments of the subject invention may, for example, process only EMG data, as EMG is easily obtained with surface sensors and may be used to implement a system which does not rely on direct brain neurological data. Each plot of FIG. 5 represents the time-frequency energy characteristics of the overall ensemble of active signals in the particular channel.

The system in the exemplary embodiment next examines the component atoms in their parameter space and compares them to parameter space representations of similar atoms in the baseline data. The baseline energy levels are considered "typical" of the background state of the subject, and changes relative to that baseline are considered to be part of the signature associated with the cued activity. The prevailing goal is to reliably compare active signals to a passive baseline period, during which the ECoG signals are assumed uncorrelated. After running a GAD process, each of the mean-parametric active condition atoms may be matched to the baseline set to determine, in effect, how often and at what energy similar atoms occur anywhere in the baseline data. For the collection of discrete baseline signals, the following calculation is preferably used to obtain $b_n$:

$$b_n^2 = \frac{1}{M}\sum_{i\in s^-}\frac{1}{N}\sum_{u=0}^{N-1}\left|\langle f^i, g_{(s_n,u,\xi_n)}\rangle\right|^2$$

The parameter $b_n$ represents the RMS baseline amplitude for the scale and frequency associated with the $n^{th}$ mean atom, and $b^2_n$ represents an estimate of the expected value of energy corresponding thereto. Each $f^i$, with i in the $s^-$ index set, represents a baseline signal in the above formula; while each g represents a Gabor atom as described in [1] and [2]. The horizontal bars each denote an average over the parameter indicated. The summation over u corresponds to a shift in position over a defined window. Using this estimate, each active-condition parametric mean atom may be re-scaled as an indication of the deviation in energy from uncorrelated baseline activity, as represented by:

$$\underline{a}_n = \frac{\overline{a}_n^2 - b_n^2}{b_n^2}.$$

To extract only the significant signal elements, the structure book of each signal in a given collection is thresholded, retaining only those atoms for which the corresponding proportionately re-scaled amplitude is larger than a fixed value $\epsilon$. This fixed value $\epsilon$ will generally be zero or larger, in the present application.

This rescaled signature extraction scheme is selected for the present exemplary embodiment specifically because the baseline data is not time correlated in the same way as the data after a cue. In other embodiments of the invention, the baseline data may be correlated and analyzed in the same way as the post-cue data here—that is, with a GAD analysis. An exemplary application of this alternative embodiment may be in searching for a finer discrimination of signatures, such as comparing movement of a finger to the movement of a thumb. In such cases where semi-controlled behavioral conditions prevail, GAD comparisons are used directly, as further also described in [1] and [2].

Figure 6:
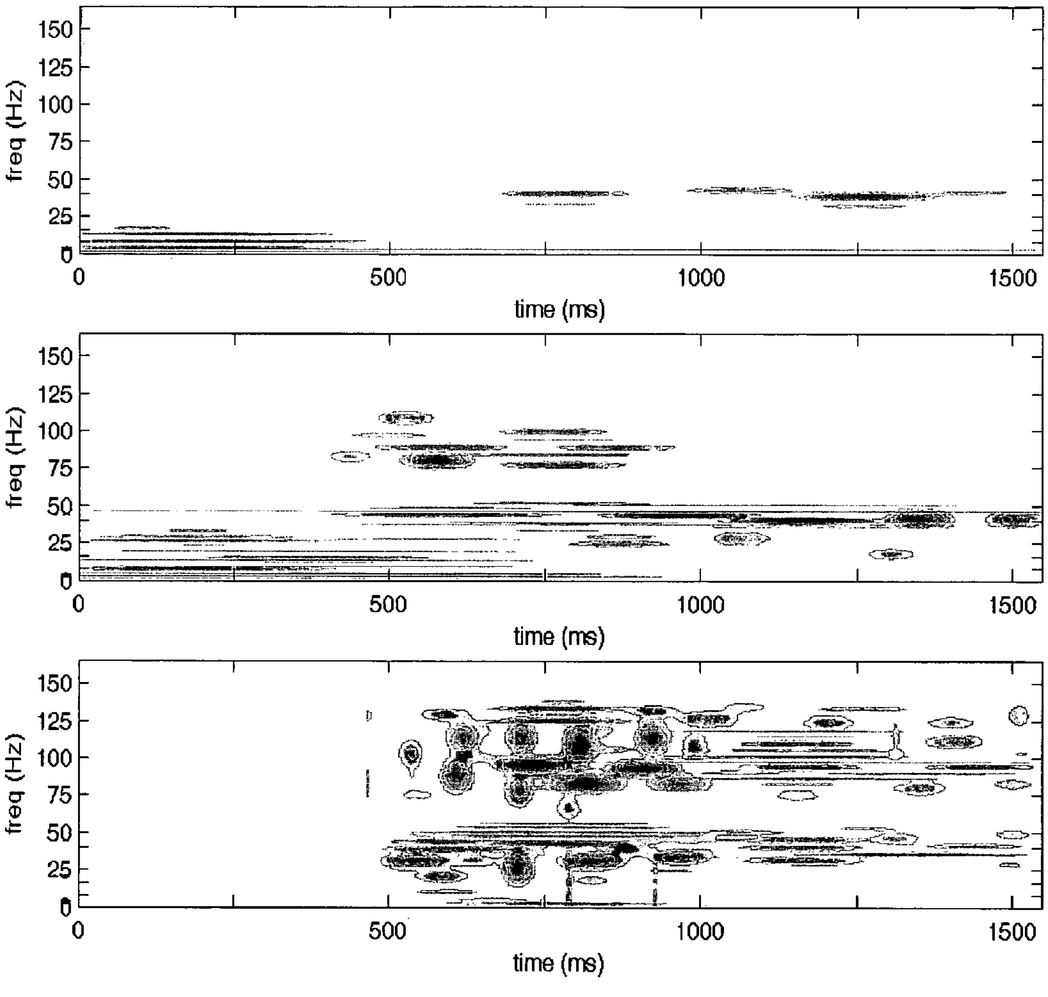
FIG. 6 is a set of graphic plots of time-frequency energy density obtained for the signal groups shown in FIG. 5, compensated with reference to a baseline condition in accordance with an exemplary embodiment of the present invention.

FIG. 6 shows the T-F energy dynamics extracted in the same example data as shown in FIG. 5, with the exemplary embodiment. These atoms reflect a weighting which effectively scales relative to baseline. Consequently, the darkness of the plane regions represents relative energy in comparison to baseline rather than an absolute measure of energy. The Recovered Detail is a time-frequency signature of the characteristics that distinguish one group of signals from another—in this case the active state from the baseline state.

In addition to ECoG, an EMG channel showing muscle activity associated with fist-clenching is also available in the given example. The EMG signal ensemble provides a direct comparison between the measured brain activity and the physical action. This aspect of the illustrated embodiment also facilitates direct exploratory comparison between the motor activity and the brain activity above.

Redundancy of information across the signal ensembles significantly speeds convergence for the disclosed method relative to other methods known in the art. All significant atoms in the present ECoG analysis are typically recovered, for instance, in less than 200 iterations. This produces a highly sparse, low dimensional representation of each signal ensemble.

For those portions of the time-frequency plane that are active, eGAD reveals striking detail when compared in resolution to results of other methods heretofore known in the art. Time-frequency correlations between the EMG and the cortical activity are easily examined in the plots. In addition, artifact signals may be isolated and easily eliminated from raw recordings that might otherwise require extra filtering steps using other methods known in the art.

As discussed in [1] and [2], the resulting representation of a signal ensemble retains phase estimates as well as localization, scale, and frequency. Significant components (thresholded in the same fashion) are summed to reconstruct a representative time-domain approximation of the signature pattern. Preferably, the recovery formula is expressed as follows:

$$\overline{f}(t) = \sum_{n_l} \overline{a}_{n_l} g_{\gamma_{n_l}}(t),$$

where the set of indexes $\{n_l\}$ represents the list of the parametric-mean atoms of interest from the analysis. The recovery formula sums over the significant atoms to reassemble a signal in the original signal space that is characteristic of what distinguishes one signal group from another. This is a signature waveform in the original signal space. In the exemplary embodiment, this signal space is defined by a waveform variable over time. The recovered signature waveforms for two analyzed channels of ECoG are illustrated in the first two plots of FIG. 7, while the time average of the EMG signal in the present example is illustrated at the bottom-most plot to show correlation with the subject's behavioral activity. In other embodiments, this signal space may be the spatial pattern over multiple electrodes, or some other suitable space of interest that is comparable to being measured by the original signal transducers.

Recovery of a signature in the original domain is not typically possible in most conventional averaging schemes because insufficient information is retained by the intervening process. For example, in schemes of prior art that use short time Fourier transforms, the averaging of coefficients provides an amplitude estimate of the time-frequency signature, but phase information is lost in the process. Hence, it is not possible to reliably recover the time domain signal without making extensive assumptions. The direct route to obtaining a representative signature signal in accordance with the present invention is a strong advantage of [1] and [2] over such conventional methods.

Figure 7:
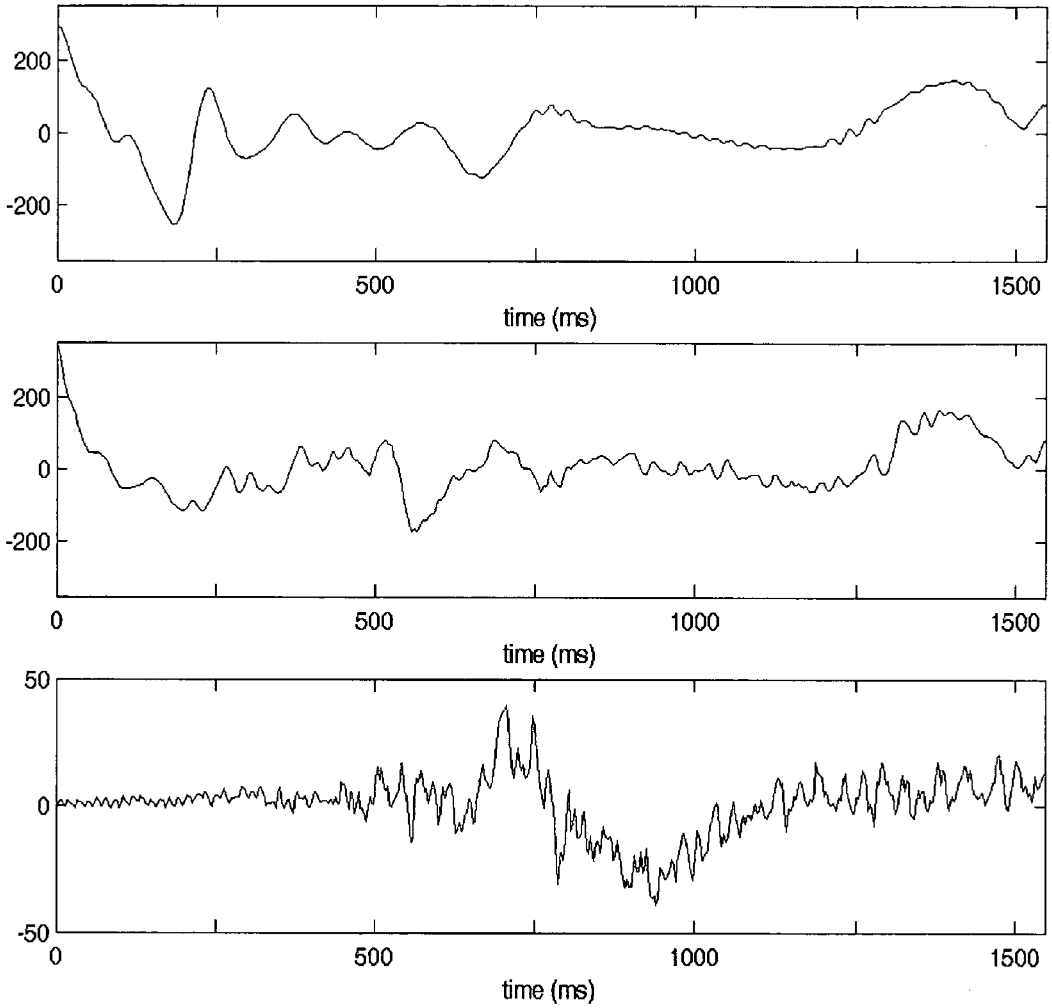
FIG. 7 is a set of graphic plots of signal waveforms recovered from the processed signal groups shown in FIG. 6, in accordance with an exemplary embodiment of the present invention.

FIG. 7 illustrates the reconstructed time-domain signals for the two ECoG channels in the present example. The time-domain average of the EMG signal is shown in the bottom-most plot for comparison with the brain activity. These plots represent an approximation to the ECoG signature activity associated with fist-clenching in this subject. Again, a notable feature of eGAD analysis in contrast to other techniques for analyzing event-related spectral changes, is that enough information is retained to reconstruct a representative time-domain signal. As demonstrated in the next example described below, this reconstructed representative signal forms a reasonable approximation of the common underlying source signal within a signal group, even when embedded in very noisy data. Hence, one may extract both spectrographic and time-domain signatures with the disclosed methods and systems.

Figure 8:
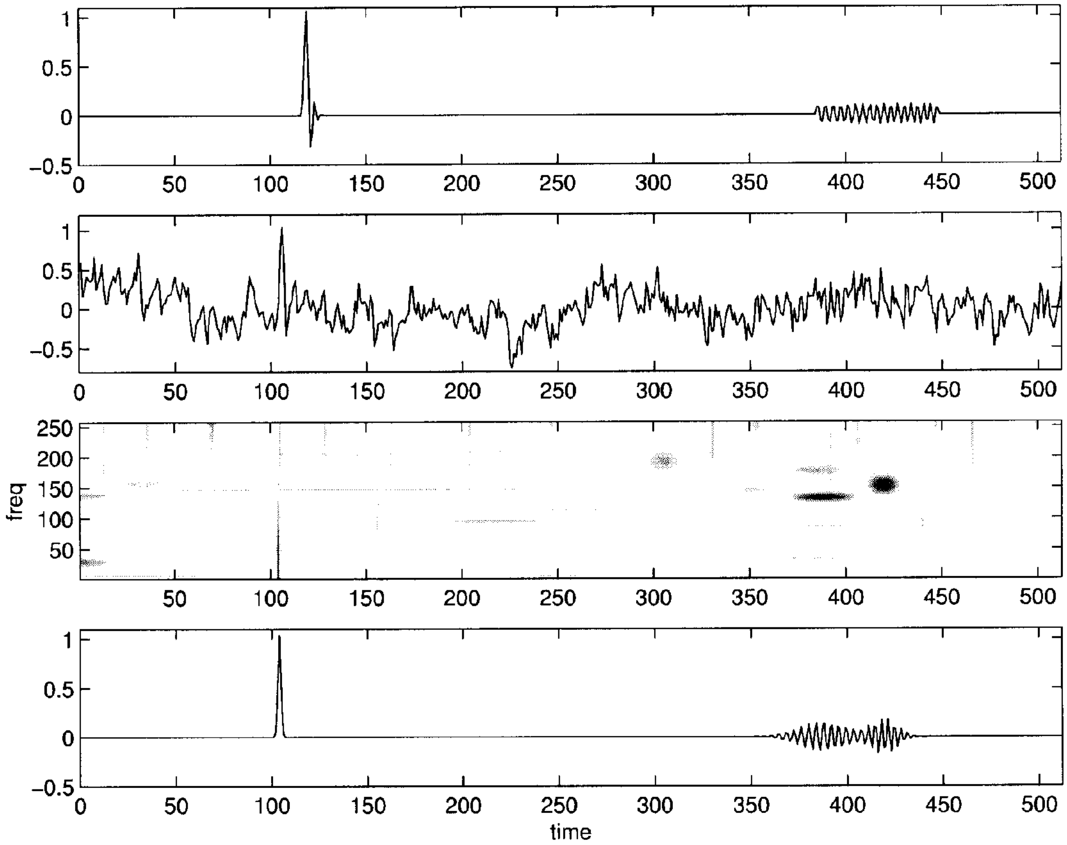
FIG. 8 is a set of graphic plots illustratively showing an isolated test signal waveform, a combined signal including the test signal embedded within noisy background, time-frequency energy densities of the combined signal as processed, and a recovered waveform obtained for the processed combined signal in accordance with an exemplary embodiment of the present invention.

FIG. 8 illustrates the results of a controlled experiment that demonstrates the effectiveness of the disclosed embodiment. A target signal is synthesized with two components, a complex transient and a portion of a rising chirp. The model signal is shown in the uppermost plot of the figure. This model signal is jittered in time by a random walk process to produce five non-time aligned copies. Each copy is embedded in 1/f noise, producing a very noisy sample. One such sample is shown in the second plot of the figure. These five samples form an ensemble of time-jittered signals with a very poor signal-tonoise ratio. With only five samples, the exemplary embodiment of the present invention is used to first recover the corresponding time-frequency characteristics (third plot) and then an approximation of the original signal in the time domain (fourth plot). The extreme noise necessarily results in some loss of detail; however, the resulting approximation retains sufficiently salient characteristics of the original model, including the precise relative time locations and duration of the signal components.

Returning to the brain signal processing example, it will be clear to those skilled in the art upon understanding this and the disclosures of [1] and [2] that once a well defined signature is extracted, it may be used in subsequent processing to detect or classify similar future events. Aspects of this are described in preceding paragraphs. Well known techniques such as matched filtering, as well as specialized dictionary methods enabled in [1] and [2] may be used for a host of applications.

The systems, processes, and methods disclosed and discussed herein are presented in the context of a specific application, namely signature processing of signals originating the brain. Upon examining and understanding the disclosure, it will be clear to those skilled in the art that similar methods may be applied to other energy mediums and to other applications.

The systems and methods may be applied to numerous applications. Some contemplated applications include for example: functional brain mapping for research and medical purposes, identification and localization of medical pathologies, brain computer interface, providing control systems for disabled patients that are tuned to the patient, human biometric identification, speechless communication and control, and the like. This list is intended to be merely exemplary and should not in anyway be construed as exhaustive. Other examples are described in [1] and [2].

Figure 9:
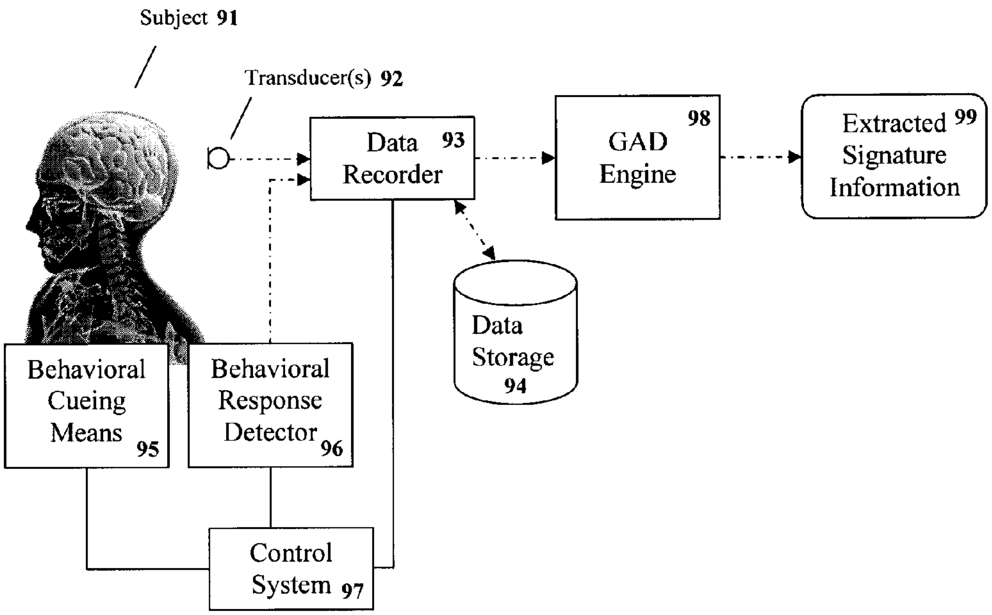
FIG. 9 is a schematic diagram illustrating a portion of a system formed in accordance with an exemplary embodiment of the present invention for developing signature information by which to discriminate neurological activity.

FIG. 9 illustrates a system formed in accordance the exemplary embodiment of the present invention described in preceding paragraphs. The system operates to collect and extract signature information/signals from a subject 91. The system effectively learns the signature information from the neurological activity observed in the subject 91 when the subject 91 exhibits or carries out certain physiological responses. System operation includes an initial training or signature extraction stage. The subject 91 is typically a human individual from whom signature patterns are learned, so that the system may be trained to monitor and track those patterns later. Depending on the intended application, the subject may also be an animal.

One or more transducers 92 are applied to the subject 91 to monitor signals from their body. The transducer(s) 92 may be any device that directly or indirectly senses neural activity, including but not limited to EEG/EcoG electrodes, standoff MEG detectors, or peripheral nerve or muscle EMG sensors applied at any suitable part of the subject's body. Measures for detecting motion and/or vibration, such as accelerometers, as well as measures of detecting acoustic, magnetic, or optical signals may also be used to gauge bio indicators of nerve activation or subject intent. Depending on the requirements of the intended application, an input transducer set may comprise one sensor, multiple sensors, or a network of sensors.

Such transducers are preferably coupled via appropriate amplifiers and preconditioning hardware (not shown) to a data recorder 93. The data recorder 93 may buffer signals internally or may store them via a data storage device 94 for later processing.

As described in preceding paragraphs, transducer sensors may be utilized individually in which case the system operates to discover only consistent signature signals in single channel data from each physical site of interest on the subject. This is an advantageous aspect of the present invention, in that reliable signature information may be extracted from only one or two applied transducers rather than relying on spatial patterns of the same. As discussed in [1] and [2], however, the system's GAD Engine 98 may operate if necessary on spatial signal groups, as well as on time-ordered signals. Hence, when multiple sensor points are available, derived signatures may comprise extracted temporal patterns, spatial patterns, or combinations thereof, which are sufficiently common to the given signals.

In order to collect signals associated with a subject's behavior or brain state, a computer-based control system 97 coordinates interoperation of system components. In certain embodiments, measures 95 are employed to cue or otherwise prompt the subject 91 to perform a specific task. Cues may comprise any suitable indicator that may be perceived by the subject, such as images or words on a computer screen, a light turning on, an audio sound, a vibration, electrical stimulation, or the like.

The behavioral task which may be monitored will depend upon the target signal. Examples include clenching or relaxing a muscle, operating a particular mechanical apparatus, making a specific movement, reading silently, uttering a specific word, imagining a specific item or situation, or any other such task of interest. In some cases, the task may be to cognitively focus upon a particular action without actually performing the action, such as imagining one's hand moving left, right, etc. In cases where the signature of interest is a particular brain state, tasks may be more passive. For example, in order to measure sleep, epileptic seizure, or anesthesia states, the states may be induced by external means or simply monitored for.

The system is not limited to a single subject. In some applications, multiple subjects may be independently monitored to seek commonalities among groups of individuals, rather than behavior specific to a particular individual. A multi-subject training embodiment is preferred when extracting signature information that is consistent across a larger population rather than specific to a single individual. Training using a broad set of typical subjects allows the GAD Engine 98 to extract signature information that generalizes across the population and increases the likelihood of a new subject subsequently being reliably monitored without the need for much if any additional subject-specific training runs.

In the embodiment shown, the system includes a behavioral response detector 96 operable to independently measure the presence, absence, or degree of the behavior or brain state of interest. This detector 96 may be coupled with the cueing measures 95 via the control system 97 to verify specific behaviors and to track timing.

The detector 96 may also be used in certain embodiments without any external cue. No external cue may be necessary, for example, where a subject is asked simply to utter a word or push a button at his or her own pace. In such embodiments, the detector 96 would trigger based upon the behavior itself.

Behavior detectors may include physical switches, knobs, encoders, audio sampling or gate trigger devices, video motion detectors, or other devices suitable for the target behavior. Behaviors of interest may also include brain states; whereupon, the detector 96 preferably comprises suitable means known in the art for detecting or gauging trauma, sleep, or anesthesia level, or for otherwise providing medical monitoring. In some cases, the detector 96 may include means to self-report brain state to the subject. The detector 96 may also comprise a human observer to manually trigger an indicator upon witnessing the desired behavior in the subject.

In other embodiments of the present invention, the system may extract markers of interest directly from the transducer data stream. This is accomplished by seeking signal dynamics which are measurable either by applying previously learned GAD-based signature detection and classification processing while searching for additional signals, or by applying suitable general signal processing means known in the art.

In general, through cueing, behavior detection, or a combination thereof, or through other suitable means, the data records of the given signals preferably include one or more timing points approximately correlated with the task or brain state of interest. These markers are used by the GAD Engine 98 in forming a course-grained alignment of signals for extraction of signature signal information.

The control system 97 coordinates recording of information and marker information in order to produce one or more collections of data recorded via the data recorder 93. These collections will include at least one set of signatures directly associated with the active behavior or brain state of interest. Each repetition of approximately similar behavior or brain state measurements produces a new trial signal that is added to the collection. In most embodiments, at least one additional collection of signals is made for comparison. This additional collection defines a baseline set of signals in which the target behavior or brain state of interest does not occur. This baseline set is used as a comparative reference by which to focus the signature extraction process, such that only those elements of the active signal collection differing sufficiently from the baseline are extracted. As discussed in [1] and [2], it is an important feature of the GAD process that very low-dimensional but precise representations of key difference may be obtained given sufficient comparison information.

In certain embodiments of the present invention, more than two collections of signals are obtained. These generally comprises sets of behaviors or brain states which are to be mutually discriminated. Examples include a subject's pushing a button using a finger, as opposed to pushing the button using a thumb; the subject's thinking of different words, such as "cat" and "dog;" the subject being under different states of anesthesia during an operation; and, the like. The present invention is not limited to any particular number of collections, although practical considerations may limit the subject having to be asked to repeat certain tasks or brain states with excessive variations. In those embodiments where multiple categories of data are collected, one category of signals may serve as a baseline for all of the other collections, or each categorical collection of signals may be compared to the other categorical collections in the aggregate.

The GAD Engine 98 is configured to carry out processing already described herein, with reference to [1] and [2]. The engine's output may comprise a collection of parameterized structure books, a parametric mean structure book, a time-frequency plane energy distribution, or a time-domain reconstruction of the typical signature associated with the specific behavior. The extracted signature information 99 is preferably a low-dimensional representation of notable elements necessary to differentiate between the groups of signals collected and processed by the system. The extracted signature information 99 may also be post-processed to group, catalog, or further reduce the information to a minimal salient set necessary to accomplish the desired detection and classification operation, as described in following paragraphs.

Figure 10:
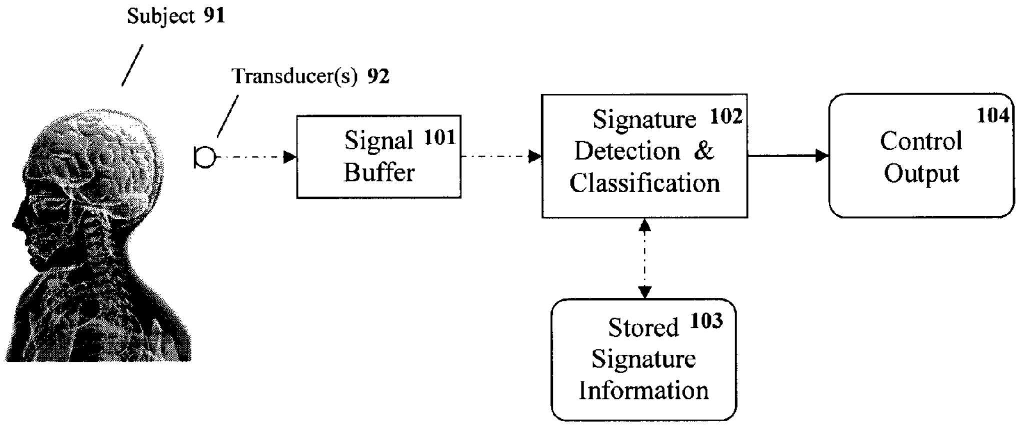
FIG. 10 is a schematic diagram illustrating a portion of a system formed in accordance with an exemplary embodiment of the present invention for monitoring signal groups to generate a control signal upon detection in accordance with the developed signature information; and, FIG. 11 is a schematic diagram illustrating a portion of a system formed in accordance with an exemplary embodiment of the present invention, as adapted for selective actuation of a control action in various illustrative control applications of the system.

FIG. 10 illustrates how the extracted information 99 is used in an exemplary embodiment to operate a detection and classification system. Again, one or more transducers 92 monitor the subject 91 as described above. The signals are passed to a signal buffer block 101 over a time window to collect a short signal vector from the data stream. Each signal vector is then transferred to block 102 where they are discriminated and classified using suitable measures described in [2], based upon stored signature information indicated at block 103.

Stored signature information 103 may comprise the information extracted in block 99 of the system. Alternatively, the information 103 may comprise post processed, filtered, cataloged, or otherwise organized combinations of such data appropriate to the control task or brain-state monitoring application of interest. Upon detection of a target signature in a novel transducer data stream, the detection at block 102 produces a control output 104. If no actionable signal is detected, the system simply waits for new input then tries again.

This control output 104 may comprise a simple trigger. The control output 104 may otherwise include more specific details, depending upon classification of the detected signature at block 102.

Figure 11:
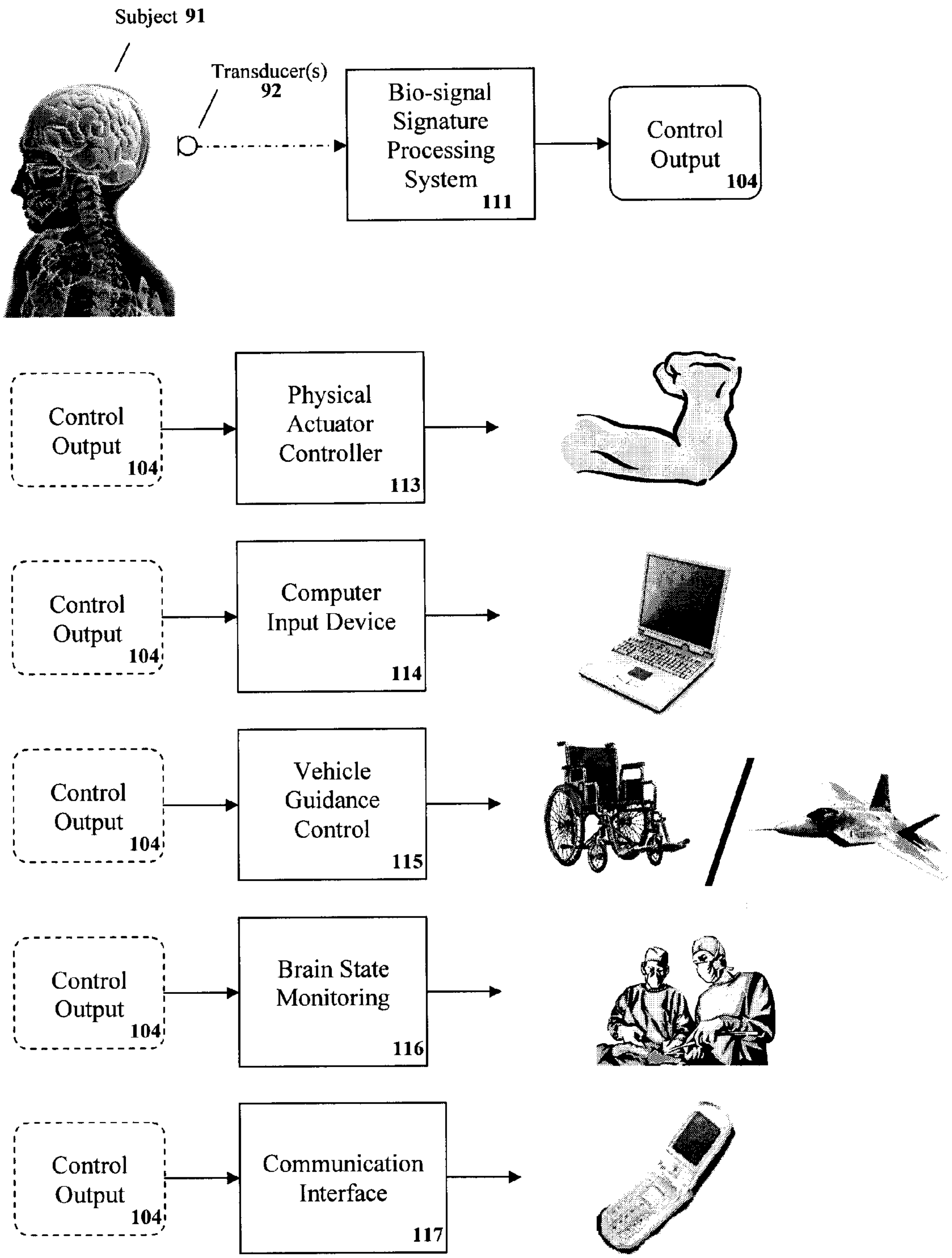

FIG. 11 illustrates exemplary applications of the system, whereby various monitoring or control actions are taken responsive to a system operating in accordance with the present invention. The detection system shown in FIG. 10 is generally referenced here by block 111. As before, processing begins with a subject 91 and transducer 92 and leads to a control output 104. An actuation interface unit 113-117 of suitable configuration, depending on the intended application, is coupled to the control output 104 to effect appropriate delivery of the control action. The control action is suitably selected according to the physiological response(s) for which the signature information was derived.

In the first exemplary application, the control output 104 activates a physical actuator 113. This embodiment may be used for remotely controlling robotic equipment, or for controlling prosthetic limbs. In this case, training of the system, as described with reference to FIG. 9, typically comprises prompting the subject to move his or her limbs; prompting the subject to simply imagine moving his or her limbs; prompting the subject to manipulate mechanical devices; or, prompting the subject to sub-vocalize or perform some other surrogate action to associate with the desired control of the target device. After training and signature extraction, the signature processing system 111 operates to detect when similar signals arise in the subject's brain and classify them to perform the appropriate physical actuator motion.

In a second example, the control output 104 serves as input to a computer via a computer input device 114. In this case, typical training might comprise prompting the subject to perform or imagine performing tasks such as manipulating a mouse, thinking of specific words, thinking of specific letters, typing, and so forth. Again, tasks might also incorporate surrogate behaviors, such as sub-vocalization or body movements, which are to be associated with the desired control of the target device. After training and signature extraction, the signature processing system 111 operates to detect when similar signals arise in the subject's brain, classify them, and generate the appropriate input signal to the general-purpose computer. This enables the subject 91 to communicate with and control the computer without physical contact or manipulation.

In a third example, the control output 104 serves as a control signal for a vehicle guidance controller 115. Again, training may include prompting the subject to perform or imagine performing tasks such as manipulating a control device, thinking of specific words, etc., or incorporating surrogate behaviors such as sub-vocalizations or limb movements to be associated with the desired control of the target device. After training and signature extraction, the signature processing system 111 operates to detect when similar signals arise in the subject brain, classify them, and generate the appropriate output signal to provide vehicle guidance. Handicapped subjects are thereby enabled to control wheelchairs or other transportation devices, and pilots or drivers are enabled to control larger vehicles. Vehicle guidance may be thus controlled by a subject 91 occupying the vehicle or remotely located therefrom.

Such control measures may also be used to supplement traditional input devices like yokes and joysticks in order provide traditional control of the vehicle in some circumstance and neural based control in others. In the latter case, the neural signals may also be used simultaneously with the traditional controls to increase response time or otherwise enhance vehicle control.

In a fourth example, the control output 104 serves as an indicator signal which reflects brain states of interest. As mentioned above, behavior in the context of the present system is contemplated to include passive brain states. Training may comprise measured anesthesia states, such that in application, the system 111 operates to provide medical personnel monitoring 116 of the subject's level of anesthesia.

Training may alternatively comprise measured states of alertness, whereby the system 111 operates during use to generate alertness monitoring alarms for drivers, pilots, soldiers, or other personnel performing critical tasks. Other applications include intoxication monitoring, detection of blackout due to environmental conditions, and medical alerts for conditions such as head trauma, concussion, coma, and seizure.

In a fifth example embodiment, the control output 104 serves to drive a communication interface 117. In this case, training may comprise similar behavioral tasks to that for computer control 114. However, in operation, the system 111 in this example detects and classifies signals to generate communications output that may be suitably transmitted, received, and decoded by other standard communications equipment. This synthesized output may be of text, synthesized speech, visual images, or any other communication format known in the art. Applications include hands free communication, silent communication, handicapped speech assistance, and the like.

The specific embodiment disclosed here are intended as an example to teach application of the subject methods of [1] and [2] to brain signal processing. Additional processing methods described in [1] and [2] will be fully applicable to brain signals and useful in additional embodiments once the relationship with the present embodiment is understood by one skilled in the art.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular combinations of method steps may be reversed or interposed, all without departing from the spirit or scope of the invention as defined in the appended claims.

What is claimed is:

1. A system for automatically correlating neurological activity to a predetermined physiological response comprising:

at least one sensor operable to sense signals indicative of the neurological activity;

a processing engine coupled to said sensor, said processing engine in a first system mode executing a simultaneous sparse approximation comprising Simultaneous Matching Pursuits, jointly upon a group of signals sensed by said sensor to generate signature information corresponding to the predetermined physiological response; and, a detector coupled to said sensors, said detector in a second system mode monitoring the sensed signals and selectively generating according to said signature information a control signal for actuating a control action according to the predetermined physiological response.

2. The system as recited in claim 1, wherein said sensor includes a transducer applied to a subject to acquire electrical signals indicative of the neurological activity.

3. The system as recited in claim 2, further comprising a transducer applied to the subject to acquire electrical muscle activity indicative of the physiological response.

4. The system as recited in claim 1, wherein said processing engine in said first system mode executes Greedy Adaptive Discrimination (GAD) processing upon the group of sensed signals.

5. The system as recited in claim 4, wherein the sensed signals in a group of sensed signals are variably aligned in time.

6. The system as recited in claim 5, further comprising a behavioral cueing unit prompting the physiological response of a subject.

7. The system as recited in claim 6, further comprising a behavioral response detector unit detecting the physiological response of a subject.

8. The system as recited in claim 4, wherein said processing engine generates said signature information based upon a parametric mean representation defined in a multi-dimensional parametric space, said parametric mean representation including a plurality of parametric mean components each independently representing a mean value within one parametric space dimension.

9. The system as recited in claim 4, further comprising an actuation interface unit coupled to the detector for performing the control action responsive to the control signal.

10. A brain-computer interfacing system for automatically correlating neurological activity of a subject to a predetermined physiological response comprising:

at least one transducer sensing signals indicative of the neurological activity;

a processing engine coupled to said transducer, said processing engine in a system training mode executing a simultaneous sparse approximation comprising Simultaneous Matching Pursuits, upon a collection of signals sensed by said transducer to generate signature information corresponding to the predetermined physiological response; and, a detector coupled to said transducer, said detector in a system utilization mode monitoring the sensed signals and generating upon detection of a sensed signal substantially characterized by said signature information a control signal for actuating a control action according to the predetermined physiological response.

11. The brain-computer interfacing system as recited in claim 10, wherein said processing engine in said first system mode executes Greedy Adaptive Discrimination (GAD) processing upon the group of sensed signals.

12. The brain-computer interfacing system as recited in claim 11, wherein said transducer is applied to a subject to acquire electrical signals indicative of the neurological activity.

13. The brain-computer interfacing system as recited in claim 12, further comprising a transducer applied to the subject to acquire electrical muscle activity indicative of the physiological response.

14. The brain-computer interfacing system as recited in claim 13, further comprising a behavioral cueing unit prompting the physiological response of a subject, and a behavioral response detector unit detecting the physiological response of a subject.

15. The brain-computer interfacing system as recited in claim 14, wherein said processing engine generates said signature information based upon a parametric mean representation defined in a multi-dimensional parametric space, said parametric mean representation including a plurality of parametric mean components each independently representing a mean value within one parametric space dimension.

16. The brain-computer interfacing system as recited in claim 15, further comprising an actuation interface unit coupled to the detector for performing the control action responsive to the control signal.

17. A method for automatically correlating neurological activity of a subject to a predetermined physiological response comprising the steps of:

actuating a sensor to sense signals indicative of the neurological activity;

executing in a processor a simultaneous sparse approximation comprising Simultaneous Matching Pursuits, jointly upon a group of the signals sensed to extract therefrom multi-dimensional signature information corresponding to the predetermined physiological response; and, monitoring subsequently sensed signals to selectively detect therefrom sensed signals substantially characterized by said signature information; and, generating a control signal responsive to said detection for actuating a control action according to the predetermined physiological response.

18. The method as recited in claim 17, further comprising the step of applying a transducer to the subject to acquire electrical muscle activity indicative of the physiological response.

19. The method as recited in claim 17, wherein said simultaneous sparse approximation executes a Greedy Adaptive Discrimination (GAD) decomposition upon the group of sensed signals, the sensed signals in each group being variably aligned in time.

20. The method as recited in claim 19, wherein said signature information is generated based upon a parametric mean representation defined in a multi-dimensional parametric space, said parametric mean representation including a plurality of parametric mean components each independently representing a mean value within one parametric space dimension.

* * * * *